(12) United States Patent
Pedrazzini

(10) Patent No.: US 8,682,475 B2
(45) Date of Patent: Mar. 25, 2014

(54) PROCESS FOR MANAGING URGENT SAMPLES IN AN AUTOMATION INSTALLATION

(75) Inventor: Gianandrea Pedrazzini, Paradiso (CH)

(73) Assignee: Inpeco Holding Ltd., Valletta (MT)

( * ) Notice: Subject to any disclaimer, the term of this patent is extended or adjusted under 35 U.S.C. 154(b) by 425 days.

(21) Appl. No.: 13/002,946

(22) PCT Filed: Jul. 10, 2009

(86) PCT No.: PCT/EP2009/058838
§ 371 (c)(1),
(2), (4) Date: Jan. 6, 2011

(87) PCT Pub. No.: WO2010/007002
PCT Pub. Date: Jan. 21, 2010

(65) Prior Publication Data
US 2011/0112683 A1    May 12, 2011

(30) Foreign Application Priority Data

Jul. 16, 2008  (IT) .............................. MI08A001290

(51) Int. Cl.
*G06F 7/00* (2006.01)
(52) U.S. Cl.
USPC ........... 700/218; 700/214; 700/213; 700/219; 700/222; 700/226; 700/230
(58) Field of Classification Search
None
See application file for complete search history.

(56) References Cited

U.S. PATENT DOCUMENTS

2005/0186113 A1* 8/2005 Koike et al. ...................... 422/63
2009/0048870 A1* 2/2009 Godshall et al. .................. 705/3

FOREIGN PATENT DOCUMENTS

| EP | 0 801 308 A2 | 10/1997 |
| EP | 1 348 965 A2 | 10/2003 |
| GB | 2 131 168 A  | 6/1984  |

* cited by examiner

*Primary Examiner* — Yolanda Jones
(74) *Attorney, Agent, or Firm* — Birch, Stewart, Kolasch & Birch, LLP

(57) ABSTRACT

A process for prioritizing urgent test tubes in a test tubes (50) transport installation is disclosed, the test tubes (50) being loaded on transport devices (4) of single test tubes (50) in an automated analysis laboratory, comprising the loading of test tubes (50) classified as urgent and non urgent on transport devices (4) for transporting single test tubes (50), moving said loaded transport devices (4) on a conveyor belt until they interact with an identification device (5) identifying the test tube upstream of processing modules (6) of the test tubes (50), removal of the test tubes (50) that are recognized to be non-urgent from the respective transport device (4) and discharging of the non-urgent test tubes (50) onto a wait bench (10) for non-urgent test tubes (50), moving transport devices (4) for transporting single urgent test tubes (50) towards the processing modules (6), the recall by a control unit (7) of the non-urgent test tubes (50) at the moment in which the availability of the processing modules (6) for non-urgent the test tubes (50) occurs and the consequent loading of the non-urgent test tubes (50) on the bench (10) onto transport devices (4) of the installation, the bench (10) providing means for locating the non-urgent waiting test tubes (50).

2 Claims, 1 Drawing Sheet

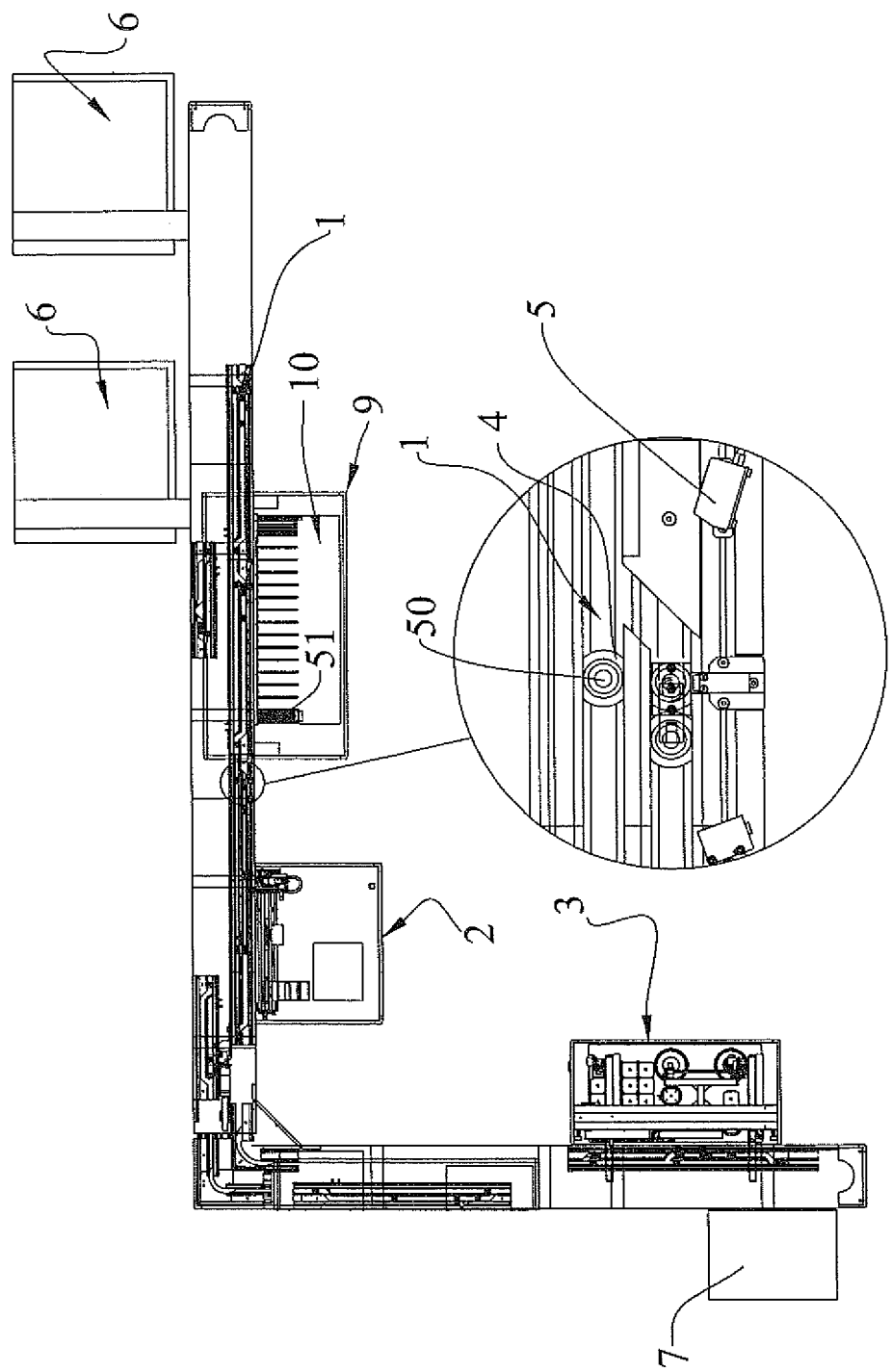

PROCESS FOR MANAGING URGENT SAMPLES IN AN AUTOMATION INSTALLATION

The present invention relates to a process for managing urgent samples in an automation installation.

Scientific progress and the development of technology have caused a great development of laboratory medicine with a consequent growth of the required analyses, in terms of both type and number.

With the introduction of automation, laboratory medicine has addressed this increase, succeeding simultaneously in accelerating analysis execution times and improving the analytical quality thereof, owing to the features of greater precision and accuracy of the automated processes.

Automation is defined as both the use of devices that are suitable for the automation of the individual stages of processing and analyzing the samples of biological material and the use of conveyors suitable for the automatic transport of such samples to said automation devices interfacing with the conveyor.

What currently still represents a potential problem inside analysis laboratories, even if they are automated, is the management of urgent cases, i.e. the management of samples of biological material that have to be processed in as short a time as possible compared with samples that, on the other hand, may be subjected to a reasonable waiting time before being processed.

This urgency generally arises from the need to obtain the report on the analyses in as short a time as possible inasmuch as the patient from whom the biological material in question has been drawn could, for example, be in the Accident and Casualty department following an emergency.

The samples that reach a laboratory, especially in the case of great dimensions that are able to conduct a wide variety of analyses, generally have different origins such as, for example, different departments of the same hospital, external hospitals or laboratories, Accident and Emergency departments, etc.

Such samples, which reach the laboratory in more or less numerous batches, are inserted inside the automation installation in random order, the identity thereof, and thus the level of urgency not being known a priori. In general, in an automation installation, the FIFO (First In, First Out) rule applies, i.e. the samples that are inserted first into the installation are the first to be processed and subsequently discharged.

Some automation installations are provided with set features, both at the software level and the hardware level, such that it is possible to assign priority to the samples once the priority thereof has been known, when they are queued behind the processing devices on the conveyor (through, for example, using preferential lanes comprised in the conveyor in which there wait a limited number of non-urgent samples on the respective transport devices).

The problem that still exists is in general the difficult management of the priorities when non-urgent samples are also physically present in the installation, occupying physical spaces such as, for example, the transport devices on the conveyor, the spaces in the containers of the centrifuges during the centrifuging stage, and generating queues that are much longer than what is expected and manageable for the various processing modules.

Thus if on the one hand software and mechanical features of the installations have been processed that are suitable for providing the priority of urgent test tubes compared with non-urgent test tubes, it has still not been possible to lower sufficiently the processing time of such urgent test tubes, thus making the use of the automation not very effective.

What could solve this limit would be an automation that is able to distinguish the urgent test tubes from the non-urgent test tubes by physically eliminating from the installation the non-urgent test tubes until the processing of the urgent test tubes has been terminated.

The object of the present invention is to make, in a laboratory automation context, a process for managing samples to be processed with urgency in order to obtain the absolute prioritization thereof with respect to non-urgent samples by physically eliminating from the installation the non-urgent samples until the conclusion of the processing of the samples, so as to overcome the problems exposed above.

According to the invention, the object is achieved with a process for prioritizing urgent test tubes in an installation for transporting test tubes that are loaded onto transport devices for transporting single test tubes to an automated analysis laboratory, characterized in that it comprises loading test tubes classified as urgent and non-urgent onto transport devices of single test tubes, the moving on a conveyor belt of said loaded transport devices until interacting with an identifying device identifying the test tube upstream of the processing modules for processing the test tubes, withdrawing the test tubes recognized as being non-urgent from the respective transport device and discharging therefrom non-urgent test tubes onto a waiting bench for non-urgent test tubes, moving transport devices of single urgent test tubes towards the processing modules, the recall by a control unit of the non-urgent test tubes in the moment in which the availability of the processing modules for the non-urgent test tubes and the consequent loading of the non-urgent test tubes waiting in the bench on transport devices of the installation occurred, the bench providing means for localizing the waiting non-urgent test tubes.

Said process is obtained through the appropriate use of the management software of the devices interfacing in the automation installation, so as to enable non-urgent samples tubes to be conveyed, for example, in suitable waiting benches or lanes positioned upstream of processing modules for processing the test tubes.

The massive identification a priori of all the samples to be processed is necessary for the consequent sorting into urgent and non-urgent samples.

The present invention represents an optimal solution for providing priority of urgent test tubes in an automatic processing chain of samples of biological material that is able to process simultaneously large quantities of test tubes.

These and other features of the present invention will be made clearer from the following detailed description of a practical embodiment thereof illustrated by way of non-limiting example in the attached drawing in which:

FIG. 1 shows a top view of an automation installation.

In FIG. 1 there is represented an example of an automation installation that is such as to enable the disclosed process to be implemented. This installation consists of a conveyor belt 1 that is suitable for receiving samples of biological material contained in test tubes, of a suitable test-tube loading device 2 or 3, for example a loading apparatus included in a pneumatic positioning installation as disclosed in Italian patent application MI2007A002255.

Once the samples contained in test tubes 50 have been loaded into the automation installation, they are inserted into suitable transport or carrier devices 4 for individual test tubes 50 and are then identified by suitable recognition devices 5, as disclosed in Italian patent application MI2007A002254.

Processing modules 6 are interfaced with the conveyor belt 1 in order to receive test tubes and process the test tubes in accordance with the requirements of a control unit 7, which is suitable for commanding and coordinating the different devices included in the automation.

In addition to the different devices interfacing with the conveyor belt 1 the process provides for there being, downstream of the sample loading devices 2 or 3, in a position below the recognition device 5, a test-tube discharging device 9 that is suitable for receiving test tubes unloaded from the installation. This discharging device 9 could consist of a bench 10 comprising multi-location racks 51 that are suitable for housing test tubes 50 in a safe and orderly manner.

The non-urgent test tube 50 is in fact removed from the carrier 4 and placed, for example, in one of said multi-location racks 51 in the bench 10.

Said device 9 ensures the traceability of the test tubes inside the device 9, simply by providing the presence of suitable software having the function of associating the code identifying the test tube read by the recognition device 5 during the loading stage and associating the code identifying the test tube with the discharging location on the bench 10.

According to what has been said, the process that is the object of the invention is explained below:

Loading stage. A batch of test tubes 50, which has reached the laboratory, is loaded onto the automation installation by the loading devices 2 or 3;

Identification stage. Once the test tubes 50 have been loaded into the installation they reach the recognition device 5 to be identified;

Recognition stage. By accessing the data on the samples contained in the test tubes 50 the control unit 7 distinguishes between the samples to be processed with urgency and the non-urgent samples;

Discharging stage. The samples that are not to be urgently processed are discharged into the test tubes 9 discharging device. The test tube 50 is removed, for example by a mechanical arm, from the carrier 4 and placed in a multi-location rack of the bench 10. The carrier 4 of the test tube 50 is now free to house another urgent test tube.

Prioritization stage. The samples to be processed urgently continue to travel on the conveyor belt 1;

End of process stage. After the processing of the urgent samples has been completed, the non-urgent test tubes waiting in the discharging device 9 can be reloaded onto the installation and processed. A control unit 20 will command the recovery of the non-urgent test tubes on the basis of various parameters such as, for example, the availability of the processing modules 6.

The disclosed process thus consists of a massive recognition of all the test tubes 50 belonging to the same batch to have reached a laboratory, distinguishing the urgent samples from the non-urgent samples and absolute prioritization of the urgent cases. This process enables very rapid sample processing times to be obtained.

The invention claimed is:

1. A process for prioritizing urgent test tubes in a transport installation of test tubes, wherein single test tubes are classified as urgent and not-urgent and are loaded on transport devices in an automated analysis laboratory, comprising the steps of:

loading the test tubes on transport devices;

transporting the test tubes which are loaded on the transport devices on a belt conveyor to an identification device;

identifying the test tubes as urgent and not-urgent which are loaded on the transport devices;

drawing of the test tubes identified as not-urgent from respective transport devices;

discharging said not-urgent test tubes onto a waiting bench;

transporting the loaded transport devices of remaining urgent test tubes to upstream processing modules;

recalling by a control unit of the not-urgent test tubes when the availability of the processing modules for the not-urgent test tubes is verified; and drawing the not-urgent test tubes on the transport device which are waiting on the waiting bench, wherein the waiting bench provides a local means for the waiting of not-urgent test tubes.

2. The process according to claim 1, wherein said waiting bench comprises multi-location containers of test tubes.